(12) United States Patent
Watanabe et al.

(10) Patent No.: US 10,191,015 B2
(45) Date of Patent: Jan. 29, 2019

(54) OBJECT INFORMATION ACQUIRING APPARATUS AND LASER APPARATUS

(71) Applicant: CANON KABUSHIKI KAISHA, Tokyo (JP)

(72) Inventors: Tadaki Watanabe, Tokyo (JP); Daisuke Nagao, Kawaguchi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/306,405

(22) Filed: Jun. 17, 2014

(65) Prior Publication Data

US 2015/0000412 A1     Jan. 1, 2015

(30) Foreign Application Priority Data

Jun. 26, 2013    (JP) ................. 2013-133815

(51) Int. Cl.
*G01N 29/24*    (2006.01)
*A61B 5/00*    (2006.01)

(52) U.S. Cl.
CPC ....... *G01N 29/2418* (2013.01); *A61B 5/0091* (2013.01); *A61B 5/0095* (2013.01);
(Continued)

(58) Field of Classification Search
CPC ........ G01N 29/24; G01N 29/00; G01N 21/00; G01N 29/2418; G01N 2291/02466;
(Continued)

(56) References Cited

U.S. PATENT DOCUMENTS 4,799,791 A * 1/1989 Echizen .............. G03F 7/70133
356/121
6,325,793 B1 * 12/2001 Tomita ................. A61F 9/008
606/10

(Continued)

FOREIGN PATENT DOCUMENTS

JP    H05-138380    6/1993
JP    H05-249657    9/1993

(Continued)

OTHER PUBLICATIONS

X. Yang et al., "Photoacoustic Tomography of Small Animal Brain with a Curved Array Transducer", *Journal of Biomedical Optics*, vol. 14, No. 5, 054007-1 through 054007-5 (Sep. 16, 2009).

(Continued)

*Primary Examiner* — Jonathan Dunlap
*Assistant Examiner* — Octavia Hollington
(74) *Attorney, Agent, or Firm* — Venable LLP

(57) ABSTRACT

An object information acquiring apparatus is used, which includes: an irradiation unit for irradiating an object with a laser beam; a restriction unit for restricting an output of the laser beam from the irradiation unit; a control unit for controlling an irradiation of the laser beam and an activation of the restriction unit; a probe for receiving acoustic waves that are generated from the object irradiated with the laser beam; and a construction unit for generating characteristic information relating to the object in use of the acoustic waves, wherein the control unit performs irradiation control of not irradiating the laser beam when the restriction unit is being activated.

14 Claims, 3 Drawing Sheets

(52) U.S. Cl.
CPC ............. *A61B 5/4312* (2013.01); *A61B 5/708* (2013.01); *G01N 2291/02466* (2013.01)

(58) Field of Classification Search
CPC .... G01H 9/00; A61B 6/00; A61B 3/10; A61B 5/00; A61B 5/0091; A61B 5/0095; A61B 5/4312; A61B 5/708; A61B 18/20; H01S 5/0687; A61F 9/008
USPC .......................................... 73/643, 627, 655
See application file for complete search history.

(56) References Cited

U.S. PATENT DOCUMENTS

| | | | |
|---|---|---|---|
| 7,329,251 B2 * | 2/2008 | Yamada | A61B 18/20 372/38.1 |
| 7,619,733 B2 * | 11/2009 | Matsumoto | G01N 21/6452 250/458.1 |
| 8,094,297 B2 * | 1/2012 | Ochiai | F22B 37/003 356/237.2 |
| 8,761,225 B2 * | 6/2014 | Ichihara | H01S 3/091 372/29.011 |
| 8,960,909 B2 * | 2/2015 | Makihira | G01J 4/00 351/206 |
| 8,970,836 B2 * | 3/2015 | Taniguchi | G01N 21/9501 356/237.2 |
| 8,991,261 B2 * | 3/2015 | Asao | A61B 5/0059 73/655 |
| 9,074,991 B2 * | 7/2015 | Suzuki | A61B 5/0095 |
| 9,585,570 B2 * | 3/2017 | Suzuki | A61B 5/0095 |
| 9,614,349 B2 * | 4/2017 | Miyata | H01S 5/02415 |
| 2001/0036207 A1 * | 11/2001 | Nagai | H01S 3/225 372/20 |
| 2010/0037695 A1 | 2/2010 | Tsujita et al. | |
| 2011/0098550 A1 | 4/2011 | Yoda | 600/407 |
| 2012/0302865 A1 * | 11/2012 | Tokita | A61B 5/0091 600/407 |
| 2012/0325006 A1 | 12/2012 | Suzuki | 73/655 |
| 2013/0116539 A1 | 5/2013 | Nagao | 600/407 |
| 2013/0338478 A1 | 12/2013 | Hirota et al. | 600/407 |
| 2014/0114169 A1 * | 4/2014 | Sato | A61B 5/0095 600/407 |
| 2014/0130600 A1 | 5/2014 | Watanabe | 73/619 |

FOREIGN PATENT DOCUMENTS

| | | |
|---|---|---|
| JP | 2000-58955 A | 2/2000 |
| JP | 2000-252551 | 9/2000 |
| JP | 2003-100653 | 4/2003 |
| JP | 2008-73341 A | 4/2008 |
| JP | 2008-221254 | 9/2008 |
| JP | 2010-022812 | 2/2010 |
| JP | 2010-42158 A | 2/2010 |
| JP | 2011-229660 | 11/2011 |
| JP | 2012-173246 | 9/2012 |
| JP | 2012-187389 | 10/2012 |

OTHER PUBLICATIONS

JPO Office Action dated Feb. 28, 2017, in counterpart Japanese patent application 2013-133815, with machine translation.
Office Action dated Jul. 17, 2018, in counterpart application JP 2017-195110 (6 pages).

* cited by examiner

OBJECT INFORMATION ACQUIRING APPARATUS AND LASER APPARATUS

BACKGROUND OF THE INVENTION

Field of the Invention

The present invention relates to an object information acquiring apparatus and a laser apparatus.

Description of the Related Art

As one type of light imaging technology using light, there is photoacoustic imaging (PAI). With photoacoustic imaging, a living body as an object is irradiated with pulsed light, and acoustic waves that are generated at an object segment, such as a tumor, based on the energy absorption of the pulsed light are received with a probe. In addition, by subjecting a reception signal output from the probe to analytical processing, optical characteristic distribution in the living body can be acquired as image data.

Japanese Patent Application Laid-Open No. 2010-022812 discloses an apparatus which holds a breast from both sides with holding members, and receives acoustic waves while a probe performs two-dimensional scanning above the holding members. As a result of using a probe to perform two-dimensional scanning, characteristic information relating to a plurality of positions in the object can be acquired.

Moreover, the technique of calculating the abundance ratio of substances with different optical absorption spectrums by using signals of acoustic waves obtained by irradiating light of a plurality of wavelengths from a laser apparatus is being researched. For example, Journal of Biomedical Optics 14(5), 054007 focuses on the point that the optical absorption spectrums are different with oxygenated hemoglobin and reduced hemoglobin existing in the blood, and describes the method of calculating the oxygen saturation in the blood by using a plurality of wavelengths.

Japanese Patent Application Laid-Open No. 2012-173246 discloses a photoacoustic apparatus in which a shutter that opens/closes to control the passing of a laser beam is provided on a light path of the laser beam between a laser light source and a biological tissue. With this apparatus, a laser beam can be stably irradiated by performing the control of closing the shutter until the laser beam is stabilized and opening the shutter at the timing of irradiating the laser beam.

Patent Literature 1: Japanese Patent Application Laid-Open No. 2010-022812
Patent Literature 2: Japanese Patent Application Laid-Open No. 2012-173246
Non-Patent Literature 1: *Journal of Biomedical Optics* 14(5), 054007

SUMMARY OF THE INVENTION

In Patent Literature 2, a shutter is provided and the shutter is closed until the laser beam becomes thermally stable, and the shutter is opened only upon measuring the photoacoustic waves in order to enable stable laser beam irradiation.

Nevertheless, when a laser is irradiated while the shutter is being opened, the laser will be irradiated in a state where the shutter is not completely open, and there was a possibility of the generation of stray light. When stray light is generated, there was a possibility of devices such as sensors configuring the apparatus malfunctioning.

The present invention was devised in view of the foregoing problems, and an object of this invention is to suppress the generation of stray light in a laser apparatus which activates a shutter to stabilize the laser beam.

The present invention provides an object information acquiring apparatus, comprising:
irradiation means configured to irradiate an object with a laser beam;
restriction means configured to restrict an output of the laser beam from the irradiation means;
control means configured to control an irradiation of the laser beam and an activation of the restriction means;
a probe configured to receive acoustic waves that are generated from the object irradiated with the laser beam; and
construction means configured to generate characteristic information relating to the object in use of the acoustic waves,
wherein the control means performs irradiation control of not irradiating the laser beam when the restriction means is being activated.

The present invention also provides a laser apparatus, comprising:
irradiation means configured to irradiate a laser beam;
restriction means configured to restrict an output of the laser beam from the irradiation means; and
control means configured to control an irradiation of the laser beam and an activation of the restriction means;
wherein the control means performs irradiation control of not irradiating the laser beam when the restriction means is being activated.

According to the present invention, it is possible to suppress the generation of stray light in a laser apparatus which activates a shutter to stabilize the laser beam.

Further features of the present invention will become apparent from the following description of exemplary embodiments with reference to the attached drawings.

DESCRIPTION OF THE EMBODIMENTS

Figure 1:
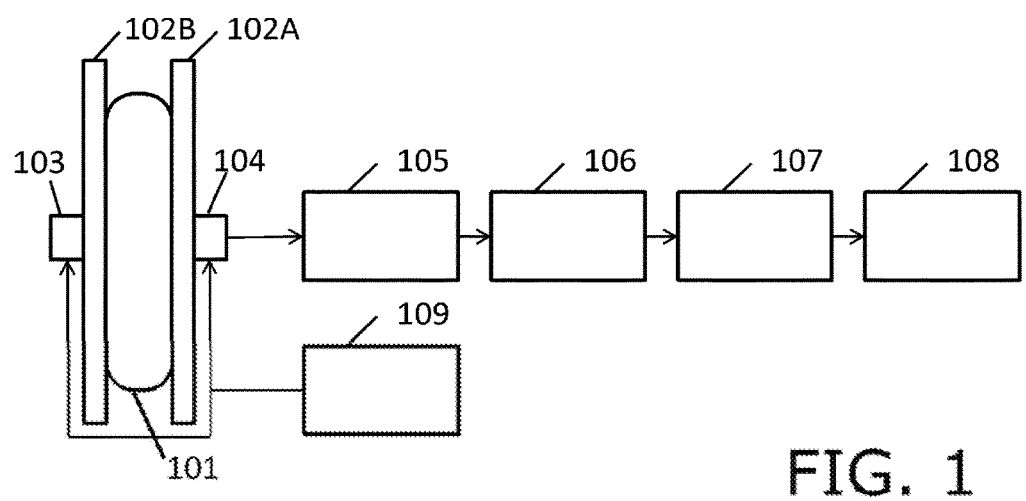
FIG. 1 is a block diagram showing the construction of the object information acquiring apparatus.

The preferred embodiments of the present invention are now explained with reference to the appended drawings. However, the size, material, shape and relative arrangement of components described below are to be suitably changed depending on the configuration and various conditions of the apparatus to which the present invention is to be applied, and these embodiments are not intended to limit the scope of the present invention to the following descriptions.

In the present invention, acoustic waves include elastic waves referred to as sound waves, ultrasound waves, photoacoustic waves, and photoacoustic ultrasonic waves, and the receiver receives acoustic waves that propagated within the object. In other words, the object information acquiring apparatus of the present invention includes an apparatus that uses the photoacoustic effect of receiving acoustic waves generated in an object by causing the object to be irradiated with light (electromagnetic waves), and acquiring the characteristic information in the object.

The characteristic information in the object acquired in the foregoing case indicates the object information which reflects the initial sound pressure of the acoustic waves that are generated based on light irradiation, the light energy absorption density derived from the initial sound pressure distribution, the absorption coefficient, or the concentration of substances configuring the tissues. The concentration of substances is, for example, the oxygen saturation or oxidized/deoxygenated hemoglobin concentration the like. Moreover, the characteristic information may also be acquired as the distribution information relating to the respective positions in the object rather than as numerical value data. In other words, distribution information such as the absorption coefficient distribution or the oxygen saturation distribution may also be acquired as image data.

The present invention is now explained in detail with reference to the drawings. Note that, as a general rule, the same constituent element is given the same reference numeral and the explanation thereof is omitted. The present invention may also be deemed an operation method or control method of an object information acquiring apparatus or a laser apparatus. The present invention may also be deemed a program for causing an information processing apparatus or the like to implement the control method. While the details are explained in the respective embodiments, the present invention is characterized in that the shutter is not activated during laser irradiation.

<Embodiment>

This embodiment explains a method of not irradiating a laser while the shutter is being activated in an apparatus which uses the photoacoustic effect.

(Basic Configuration of Apparatus)

FIG. 1 is a block diagram showing the configuration of the object information acquiring apparatus in this embodiment.

The object information acquiring apparatus comprises holding members 102 for holding an object 101 such as a living body, an irradiation unit 103 for irradiating light, and a probe 104 as a receiver for receiving acoustic waves and converting the received acoustic waves into reception signals. The object information acquiring apparatus further comprises a measuring unit 105 for amplifying the reception signals and converting the amplified reception signals into digital signals, a signal processing unit 106 for performing integration processing and the like of the digitalized reception signals, and an image construction unit 107 for generating image data from output signals from the signal processing unit. The object information acquiring apparatus further comprises an image display unit 108 for displaying an image generated with the image construction unit 107, and a scanning control unit 109 for moving the irradiation unit 103 and the probe 104.

The respective blocks are now explained in detail.

(Holding Members)

As the object 101, considered may be, for example, abreast of a living body. The holding members 102 are configured from a pair of holding members; namely, a first holding member 102A and a second holding member 102B for holding the object 101 from either side. The relative position of both holding members is controlled with a holding mechanism not shown in order to change the holding gap and holding pressure. In the ensuing explanation, when there is no need to differentiate the holding members 102A and 102B, they will be collectively indicated as the holding members 102.

The object 101 is fixed as a result of the holding members 102 sandwiching the object 101, and the measurement error caused by the movement of the object 101 is thereby reduced. Moreover, the object 101 can be adjusted to the intended thickness in accordance with the penetration depth of light. Note that, since the holding member 102B is positioned on the light path of light, it is preferably configured from a material, such as polymethylpentene, with high transmittance relative to the used light. Moreover, the holding member 102A on the side of the probe 104 is preferably configured from a member with high acoustic consistency with the probe 104.

The user opens a door not shown provided to a cabinet and performs procedures for holding the object 101, and thereafter fixes the holding members 102, closes the door, and starts the photography.

(Irradiation Unit)

The irradiation unit 103 for irradiating the object 101 with light is configured from a light source for generating light, and an irradiation part for irradiating the object with light from the light source by guiding light to that object. The irradiation unit corresponds to the irradiation means of the present invention.

As the light source, preferably used is a solid-state laser capable of generating pulsed light (pulse width of 100 nsec or less) having a center wavelength in a near infrared region of 530 to 1300 nm. For example, a Yttrium-Aluminium-Garnet laser or a Titan-Sapphire laser is used. Note that the light emission wavelength is switched between 530 nm and 1300 nm according to the light absorbing substance (for instance, hemoglobin or glucose, or cholesterol) in the object to be measured.

The light source is configured from a pulse-forming network, a flash lamp, a laser medium, a Q-switch, wavelength switching means, a variable voltage power source, voltage control means, light irradiation restriction means, light irradiation restriction activating means, and light irradiation restriction control means.

In the voltage control means, the variable voltage power source is controlled, and the pulse-forming network accumulates an electrical charge according to the voltage of the variable voltage power source, and generates a high current pulse from the accumulated electric charge. In addition, the high current pulse from the pulse-forming network is sent to the flash lamp and, by consequently exciting the laser medium, a laser beam is emitted.

Here, the Q-switch implements Q-switching and outputs a giant pulse from the excited laser medium.

The light irradiation restriction means (a shutter in this example) is disposed on an exit end side on the light path in order to prevent the output of the laser from the irradiation unit described later, and completely blocks the light when it is closed, and light is output when it is open. The light irradiation restriction means corresponds to the restriction means of the present invention.

The light irradiation restriction means is controlled by the light irradiation restriction activating means. The light irradiation restriction control means monitors the light irradiation activating means, and additionally notifies the voltage control means or the Q-switch to suppress the laser output. The light irradiation restriction activating means corresponds to the power source for activating the shutter. The light irradiation restriction control means corresponds to an information processing apparatus or a circuit that gives an activation instruction of the power source. The light irradiation restriction control means corresponds to one function of the control means of the present invention.

The wavelength used in the wavelength switching means is changed. An unstable laser beam that is generated when the used wavelength is changed is blocked by the light irradiation restriction means, and only an effective laser beam is used. Thus, when the wavelength is changed, the light irradiation control means is caused to be a closed state in order to restrict the laser output. The light irradiation restriction means is also used for output control in an state where the laser is unstable at the start of light irradiation.

Figure 3:
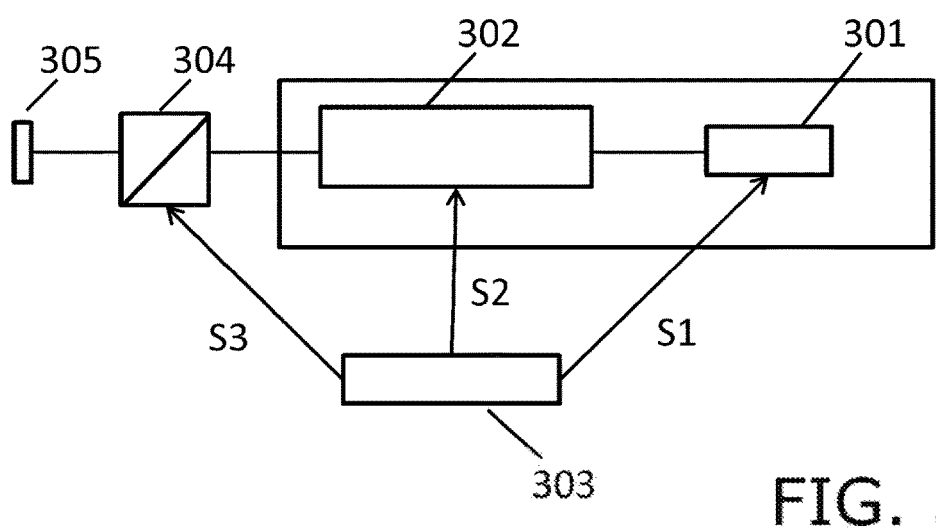
FIG. 3 is a schematic diagram showing the construction of the laser apparatus.

Among these constituent elements, the main parts are shown in FIG. 3. The control controller 303 controls the overall apparatus. When the laser medium 301 is irradiated with excitation light from a flash lamp (not shown) and becomes an inverted distribution state, a laser irradiation instruction S1 from the control controller 303 is received and laser is thereby irradiated. The irradiation instruction is given, for example, via Q-switching.

Here, by outputting a wavelength change instruction S2 to the wavelength switching means 302, the intended wavelength can be selected. The wavelength can be selected based on known methods such as by using a filter or a prism. Moreover, when the light irradiation restriction means 304 as the shutter is closed based on an open/close instruction S3, light is not output from the output coupler 305.

However, when the light irradiation restriction means is a mechanical shutter, a given length of time is required for the open/close operation. Thus, when light is irradiated before the shutter is completely open or before the shutter is completely closed after receiving the open/close instruction, at least a part of the light may become stray light. For example, when the irradiation frequency of the pulsed laser beam is 20 Hz and 100 ms is required as the time for the operation of opening the shutter, the laser will be irradiated midway while the shutter is being opened. Then, the control of the present invention is required.

In the ensuing explanation, the method of activating the light irradiation restriction means upon switching the wavelength of the laser to be used and thereby restricting the laser output is explained with reference to the flowchart of FIG. 2.

Figure 2:
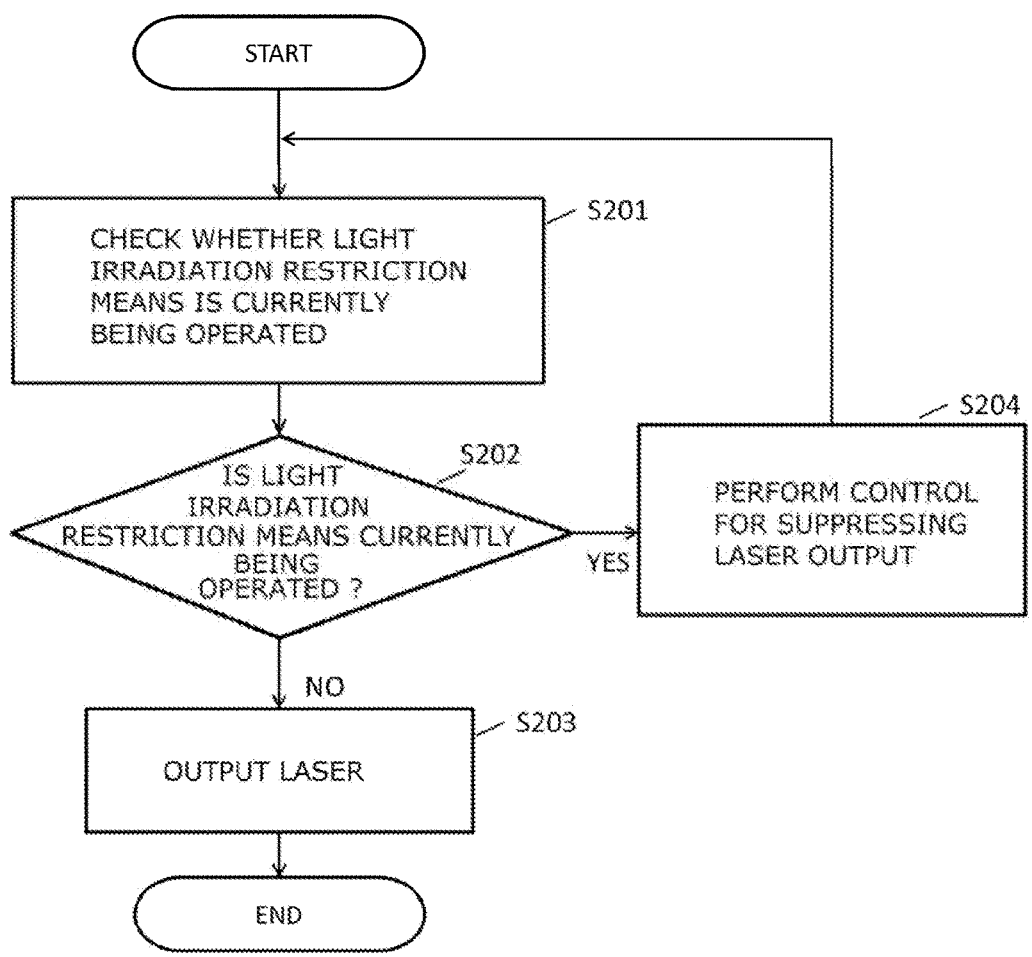
FIG. 2 is a flowchart showing an example of restricting the irradiation when the shutter is being activated.

FIG. 2 is started at the time of switching the wavelength.

Foremost, in step S201, whether the light irradiation restriction control means is currently activating the light irradiation restriction means is checked. Here, as a method of determining whether the light irradiation restriction means is being activated, there is the method of the light irradiation restriction activating means using a sensor or the like to monitor whether the light irradiation control means is being activated. Moreover, when the light irradiation restriction activating means is periodically activating the light irradiation control means, the method of checking the periodic interval with the light irradiation restriction control means may also be adopted.

Subsequently, in step S202, whether the light irradiation restriction means is being activated is determined.

When the determination result is NO (not being activated), the routine proceeds to step S203, and the voltage control means controls the variable voltage power source and outputs the laser.

Meanwhile, when the determination result is YES (being activated), the routine proceeds to step S204, and control for suppressing the laser output is performed. Foremost, the light irradiation restriction control means notifies the voltage control means or the Q-switch to stop the laser output. The voltage control means or the Q-switch that received the foregoing notice performs control for suppressing the laser output.

The specific control of the voltage control means in S204 is the method of suppressing the input of voltage from the variable voltage power source to the pulse-forming network, or the method of suppressing the application of a pulse to the flash lamp. Moreover, as the control of the Q-switch, considered may be the method of prohibiting Q-switching that is performed for outputting the laser output. The configuration may also be such that the notice for stopping the laser output from the light irradiation restriction control means is sent to either the voltage control means or the Q-switch, or sent to both the voltage control means and the Q-switch.

In particular, the method of suppressing the application of voltage from the variable voltage power source to the pulse-forming network can more reliably restrict the output of laser since the laser medium is not excited to begin with.

Moreover, rather than the foregoing control of completely stopping the laser output, for instance, the configuration may also be such that the application of voltage from the variable voltage power source to the pulse-forming network is reduced to gradually reduce the laser output and weaken the stray light.

While this embodiment explained an example of performing control for restricting the laser emission during the open/close operation of the light irradiation control means upon switching the wavelength switching, the foregoing control of restricting the laser emission may also be performed during the open/close operation of the light irradiation control means other than upon switching the wavelength.

A light source normally has a preset irradiation frequency. This is set as a design value for continuously irradiating pulsed light of the intended intensity. Since this irradiation frequency affects the number of times that photoacoustic measurement can be performed per unit time, the higher the irradiation frequency, the better.

As the irradiating part, used may be, for example, a mirror that reflects light, a lens that condenses or expands light or changes the shape thereof, a prism that scatters, bends or reflects light, an optical fiber that propagates light, or a diffuser. The irradiating part may be any kind of component so as long as the intended area of the object is irradiated with light emitted from the light source in an intended shape.

(Probe)

The probe 104 comprises an element for receiving acoustic waves and converting the received acoustic waves into electrical signals (reception signals). As the element of the probe 104, considered may be a conversion element that uses the piezoelectric phenomena, a conversion element that uses the resonance of light, or a conversion element that uses the change in capacitance. Any kinds of element so as long as it can receive acoustic waves and convert the received acoustic waves into electrical signals. The use of a probe in which a plurality of elements are disposed one-dimensionally or two-dimensionally is preferable since the measurement can be enlarged, the measurement time can be shortened, and the SN ratio can be improved.

Note that, since the sound pressure of the generated acoustic waves is proportional to the light intensity of light, the area of the front face of the probe is preferably irradiated in order to improve the SN ratio of the reception signals. Thus, the exit end of light of the irradiation unit 103 and the probe 104 are preferably disposed at positions facing each other across the object. Moreover, the scanning control unit 109 preferably performs scanning in synch so as to maintain the positional relationship of the exit end of light and the probe 104. Moreover, as a result of the irradiating part also guiding light to the side of the probe 104, the object 101 can be irradiated with light from the same side as the probe 104.

(Measuring Unit)

The measuring unit 105 is configured from a signal amplification unit for amplifying analog signals (analog reception signals) that are input from the probe 104, and an A/D converter for converting the analog signals into digital signals. The signal amplification unit performs control of increasing or decreasing the amplification gain according to the time from the irradiation of light until the acoustic waves reach the element of the probe in order to obtain image data with an even contrast regardless of the depth in the object.

(Signal Processing Unit)

The signal processing unit 106 corrects the sensitivity variation of the element relative to the digital reception signals output from the measuring unit 105, performs compensation processing of a physically or electrically defective element, performs recording operation to a recording medium not shown, performs integration processing for noise reduction, and so on. The integration processing is performed for reducing the system noise by repeatedly receiving acoustic waves at the same scanning position relative to the object 101 and performing averaging processing of the reception signals, and thereby improving the SN ratio of the reception signals.

(Image Construction Unit)

The image construction unit 107 uses the signals output from the signal processing unit 106 and acquires, as image data, the distribution (characteristic distribution such as absorption coefficient distribution and oxygen saturation distribution) that indicates the optical characteristic information relating to the respective positions in the object 101. Moreover, various types of correction processing such as brightness adjustment, distortion correction or cutout of attention area may be performed to the generated image data in order to obtain image data that is more suitable for diagnosis. The image construction unit corresponds to the construction means of the present invention. The construction means of the present invention can include functions of the above-mentioned measuring unit and signal processing unit.

(Image Display Unit)

The image display unit 108 receives the input of image data from the image construction unit 107, and displays an image of the characteristic distribution.

(Scanning Control Unit)

The scanning control unit 109 controls the scanning position of the exit end of light and the probe 104 as described above. As a result of performing two-dimensional scanning to the object 101 and receiving the acoustic waves at the respective scanning positions, broad characteristic information can be acquired even with a small probe.

While this embodiment adopted a configuration of receiving acoustic waves by performing scanning with the irradiation unit 103 and the probe 104 above the holding member 102, this embodiment can also be applied to an apparatus that manually performs scanning with the probe and performs photoacoustic measuring by using a plurality of wavelengths.

When this embodiment is applied to an apparatus that manually performs scanning with the probe and performs photoacoustic measurement, it is possible to prevent the object from being irradiated with unwanted irradiation light that is not used for the measurement pursuant to the wavelength switching. Particularly when the object is a living body, the irradiation of unwanted light needs to be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-133815, filed on Jun. 26, 2013, which is hereby incorporated by reference herein in its entirety.

What is claimed is:

1. An object information acquiring apparatus comprising:
   irradiation means configured to irradiate an object with a laser beam;
   a shutter unit having a shutter disposed on a light path of the laser beam from the irradiation means to the object, configured to restrict an output of the laser beam from the irradiation means to the object;
   control means configured to control an irradiation of the laser beam by the irradiation means and an operation of the shutter unit;
   a probe configured to receive an acoustic wave generated from the object irradiated with the laser beam; and
   construction means configured to generate, using the acoustic wave, characteristic information relating to the object,
   wherein the irradiation means is configured to generate the laser beam at a plurality of wavelengths and to irradiate the laser beam with a wavelength selected from among the plurality of wavelengths, and
   wherein the control means performs, while the wavelength of the laser beam is switched, a control of closing the shutter and a control of stopping or suppressing the generation of the laser beam by the irradiation means.

2. The object information acquiring apparatus according to claim 1, wherein the irradiation means irradiates a laser beam as a result of excitation of a laser medium by a flash lamp that has received a pulse formed in a pulse-forming network, and also as a result of Q-switching of the laser medium by a Q-switch.

3. The object information acquiring apparatus according to claim 2, wherein the control means stops or suppresses the laser output of the irradiation means by suppressing an input of a voltage to the pulse-forming network.

4. The object information acquiring apparatus according to claim 2, wherein the control means stops or suppresses the laser output of the irradiation means by suppressing an application of a pulse to the flash lamp.

5. The object information acquiring apparatus according to claim 2, wherein the control means stops or suppresses the laser output of the irradiation means by prohibiting the Q-switch from implementing Q-switching.

6. The object information acquiring apparatus according to claim 1, wherein the shutter unit comprises a mechanical shutter.

7. The object information acquiring apparatus according to claim 6, wherein the mechanical shutter requires a given length of time for the opening/a closing operation.

8. The object information acquiring apparatus according to claim 1, wherein stray light due to irradiation of the laser beam into the shutter unit while the shutter unit is operation of opening/closing is reduced.

9. A method of controlling an object information acquiring apparatus having irradiation means configured to irradiate an object with a laser beam and further to switch wavelength of the laser beam, a shutter unit having a shutter disposed on a light path of the laser beam from the irradiation means to the object, the method comprising:
   performing, while the wavelength of the laser beam is switched, a control of closing the shutter and a control of stopping or suppressing generation of the laser beam by the irradiation means.

10. The method according to claim 9, wherein irradiating the object with the laser beam comprises exciting a laser medium by a flash lamp that has received a pulse formed in a pulse-forming network and Q-switching the laser medium by a Q-switch.

11. The method according to claim 10, wherein stopping or suppressing the laser output comprises suppressing an input of a voltage to the pulse-forming network.

12. The method according to claim 10, wherein stopping or suppressing the laser output comprises suppressing an application of a pulse to the flash lamp.

13. The method according to claim 10, wherein stopping or suppressing the laser output comprises prohibiting the Q-switch from implementing Q-switching.

14. The method according to claim 9, wherein stray light due to irradiation of the laser beam into the shutter unit while the shutter unit is opening/closing is reduced by stopping or suppressing the laser output of the irradiation means.

* * * * *